United States Patent
Alfano et al.

(10) Patent No.: US 10,900,954 B2
(45) Date of Patent: Jan. 26, 2021

(54) METHOD AND SYSTEM FOR INDUCING CONTROLLED AND VARIED FLUID STRESSES BY BEAD OSCILLATION

(71) Applicant: BLAZE MEDICAL DEVICES, INC., Ann Arbor, MI (US)

(72) Inventors: Kenneth Alfano, Canton, MI (US); Michael Tarasev, Pinckney, MI (US); Sumita Chakraborty, Ann Arbor, MI (US)

(73) Assignee: Blaze Medical Devices, Inc., Ann Arbor, MI (US)

( * ) Notice: Subject to any disclaimer, the term of this patent is extended or adjusted under 35 U.S.C. 154(b) by 57 days.

(21) Appl. No.: 15/098,228

(22) Filed: Apr. 13, 2016

(65) Prior Publication Data

US 2016/0305929 A1   Oct. 20, 2016

Related U.S. Application Data

(60) Provisional application No. 62/147,567, filed on Apr. 14, 2015.

(51) Int. Cl.
*G01N 33/49* (2006.01)

(52) U.S. Cl.
CPC ..... *G01N 33/49* (2013.01); *G01N 2203/0089* (2013.01)

(58) Field of Classification Search
CPC .. G01N 3/00; G01N 33/49; G01N 2230/0089; C12N 5/0634; C12N 5/0641
See application file for complete search history.

(56) References Cited

U.S. PATENT DOCUMENTS

| | | |
|---|---|---|
| 6,659,637 B2 | 12/2003 | Friedman |
| 7,790,464 B2 | 9/2010 | Tarasev |
| 8,142,067 B2 | 3/2012 | Dorado Gonzalez et al. |
| 8,268,244 B2 | 9/2012 | Tarasev et al. |
| 2006/0121603 A1 | 6/2006 | Yuan et al. |
| 2010/0151512 A1 | 6/2010 | Huemer |
| 2010/0184120 A1* | 7/2010 | Tarasev ................ G01N 33/721 435/29 |
| 2010/0282059 A1 | 11/2010 | Van Dyke-Restifo et al. |
| 2011/0300574 A1 | 12/2011 | Tarasev et al. |
| 2012/0178121 A1 | 7/2012 | Tarasev et al. |
| 2013/0041239 A1* | 2/2013 | Sofer .................. G01N 33/84 600/323 |
| 2016/0011171 A1* | 1/2016 | Alfano .................. G01N 33/49 435/29 |

FOREIGN PATENT DOCUMENTS

| | | |
|---|---|---|
| WO | 01/58432 A1 | 8/2001 |
| WO | 2005/077511 A2 | 8/2005 |
| WO | 2008/104916 A2 | 9/2008 |
| WO | 2014/137499 A1 | 9/2014 |

OTHER PUBLICATIONS

Raval et al, Vox Sanguinis, 2010, 99, 325-331, "The use of the mechanical fragility test in evaluating sublethal RBC injury during storage" (Year: 2010).*
Baskurt, Oguz K., Red Blood Cell Mechanical Stability, (Scientific Research Journal) Engineering, 2012, 5, pp. 8-10, (Published Online Oct. 2012 (http://www.SciRP.org/journal/eng).
Gu, Lei et al., Mechanical Fragility Calibration of Red Blood Cells, American Society of Artificial Internal Organs Journal, ASAIO J. May/Jun. 2005—vol. 51—Issue 3—pp. 194-201.
Kameneva, Marina V., et al., Mechanical Trauma to Blood, in: O.K.Baskurt, M.R.Hardeman, M.W.Rampling and H.J.Meiselman (Eds.), Handbook of Hemorheology and Hemodynamics, Amsterdam, Berlin, Oxford, Tokyo, Washington DC, 2007, pp. 206-227.
Harm, Sarah K. et al, Changes in Mechanical Fragility and Free Hemoglobin Levels after Processing Salvaged Cardiopulmonary Bypass Circuit Blood with a Modified Ultrafiltration Device, Journal of Extra-Corporeal Technology; 44, 1; pp. 21-25; Perfusion downunder by American Society of ExtraCorporeal Technology; 2012.
Blackshear, Perry L., Jr., Mechanical Hemolysis in Flowing Blood, Biomechanics Its Foundations and Objectives, 1972, pp. 501-525, Chapter 19, Prentice Hall, Inc., Englewood Cliffs, N.J.
Hodgson, G. W. et al, The Pipeline Flow of Capsules Part 1: The Concept of Capsule Pipelining, The Canadian Journal of Chemical Engineering, Apr. 1963, pp. 43-45.
Charles, M. E., The Pipeline Flow of Capsules Part 2: Theoretical Analysis of the Concentric Flow of Cylindrical Forms, The Canadian Journal of Chemical Engineering, Apr. 1963, pp. 46-51.
Kameneva, Marina V. et al., Effects of Turbulent Stresses upon Mechanical Hemolysis: Experimental and Computational Analysis, ASAIO Journal 2004, Apr. 2004, pp. 418-423, McGowan Institute for Regenerative Medicine, Pittsburgh, PA.
Kameneva, Marina V. et al., Plasma Protective Effect on Red Blood Cells Exposed to Mechanical Stress, ASAIO Journal 1997, Sep.-Oct. 1997;43(5):M571-5, (5 pages), McGowan Center for Artificial Organ Development, Pittsburgh, PA.

* cited by examiner

*Primary Examiner* — Ruth A Davis
(74) *Attorney, Agent, or Firm* — Reising Ethington P.C.

(57) ABSTRACT

A method using variable bead-oscillation-based stress parameters, including relative bead dimensionality or other structural features as well as stress duration or intensity or overall magnitude, in inducing different shear stresses in biological samples, for testing the effects of different combinations of various defined stress conditions.

6 Claims, 7 Drawing Sheets

Figure 1A:
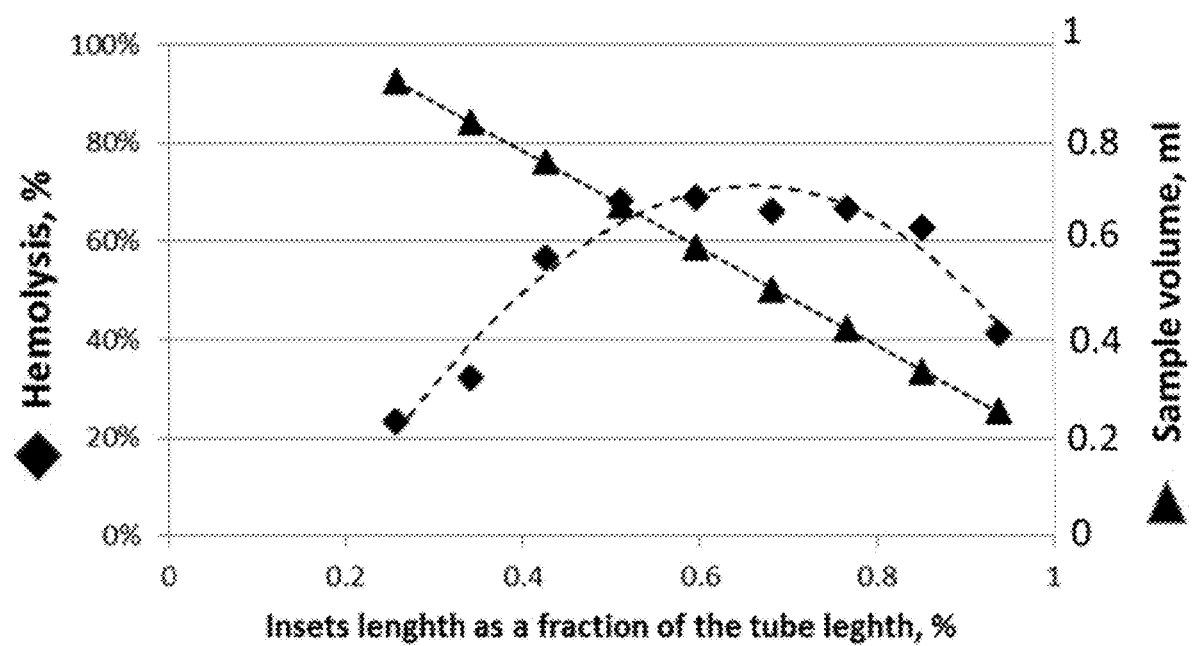

METHOD AND SYSTEM FOR INDUCING CONTROLLED AND VARIED FLUID STRESSES BY BEAD OSCILLATION

CROSS-REFERENCE TO RELATED APPLICATIONS

This application claims priority to U.S. provisional patent application No. 62/147,567, filed 14 Apr. 2015, which is hereby incorporated by reference as though fully set forth herein.

FIELD

This disclosure relates to research and testing. More particularly, it relates to testing the effects of mechanical stress on liquid sample, especially biological sample such as whole blood or any components thereof such as red blood cells (RBC), and particularly involving shear stress.

BACKGROUND

This section contains relevant background material which is not necessarily prior art.

Bead mills are common devices for disrupting sample, typically biological sample, and their objective is generally to rapidly and fully disrupt a sample using mechanical stresses associated with some sort of bead agitation or oscillation in a tube or container holding a sample. However, there are various applications, particularly in biomedical and life science areas, where it can be desirable to subject samples to stresses whose parameters are controlled. While commercial bead mills may have timers allowing some control over the overall stressing duration, as well as oscillation-frequency settings allowing some control over the stressing intensity, the particular nature of stresses being applied to the samples are not generally well characterized nor are the bead mills designed to facilitate targeting one type(s) of stress more than other(s).

International patent application publication WO/2014/137499 ("Bead Mill and Method of Use"), which has since also been filed as U.S. (national stage) application Ser. No. 14/773,137 and published as US20160011171 A1, the disclosures of which are hereby incorporated by reference in their entirety, includes a description of a bead milling system and method in which an object oscillates longitudinally in a container holding a sample, and certain stressing parameters can be separately controlled by using a bead that is magnetically moved within a sample/cartridge and allowing the user to determine the oscillation frequency as well as the magnetic force applied. It also indicated that the biochemical environment of a sample during the testing potentially impacts the effective stress experienced by a specimen (i.e. lysis efficiency, if lysing cells). Also described was the use of a non-spherical bead, particularly cylindrical (noting that it provided higher lysing efficiency in the context of stressing cells), as well as select non-conventional beads such as with ridges/grooves or a knurled surface or multiple concentric/coaxial hallow cylinders (likewise for lysing efficiency purposes, i.e. enhancing overall stress magnitude at given parameters).

SUMMARY

This section briefly and non-exhaustively summarizes subject matter of this disclosure.

The present disclosure now addresses using different bead-oscillation-based stress parameters, including bead dimensionality and shape, including non-spherical and essentially cylindrical, to induce qualitatively as well as quantitatively different stresses in samples. Other variable stress parameters may include overall stress magnitude as well as separated components thereof—such as duration and factors contributing to intensity. Depending upon the nature of the particular sample being tested, any subsequent analysis after the stressing may include a range of biochemical and/or biomechanical assays that could then aid in ascertaining the effects of any given combination of stress parameters upon respective samples run.

Bead design, particularly relative to the container/cartridge interior in which the sample resides during stressing/testing, can in some cases play a significant role in determining the relative contribution of turbulent and laminar flow based stress induced. By exploiting such phenomena, appropriate beads/objects can be identified or produced, and employed in testing samples so as to create (or come usefully close to) stress conditions desired in a given instance.

A notable example application occurs with testing red blood cell (RBC) mechanical fragility (MF), in which a sample containing RBC is subjected to mechanical stress of defined amount(s) after which the level of hemolysis in said sample is measured to reflect the MF of the cell population. While turbulence has been noted as a relevant factor in blood circulation and related issues, the ability to meaningfully control the relative or absolute amount and/or nature of turbulence, in addition to overall stress control, has short-term utility as a research tool/technique (e.g. as an enhancement to MF testing) and potential long-term utility in medical product development or medical practice (potential areas of adoption for routine MF testing in general). US patent application publication US20100184120 A1 ("Apparatus and method to characterize blood and red blood cells via erythrocyte membrane fragility quantification") and descendant filings, the disclosures of which are hereby incorporated by reference in their entirety, include a description of a generalized multi-parameter approach to testing RBC MF.

DRAWINGS

This section briefly describes accompanying drawings for this disclosure.

FIGS. 1A-1D include experimental data showing how the protective effect of albumin upon RBC during MF testing depends upon the shape of the bead employed.

Figure 2A:
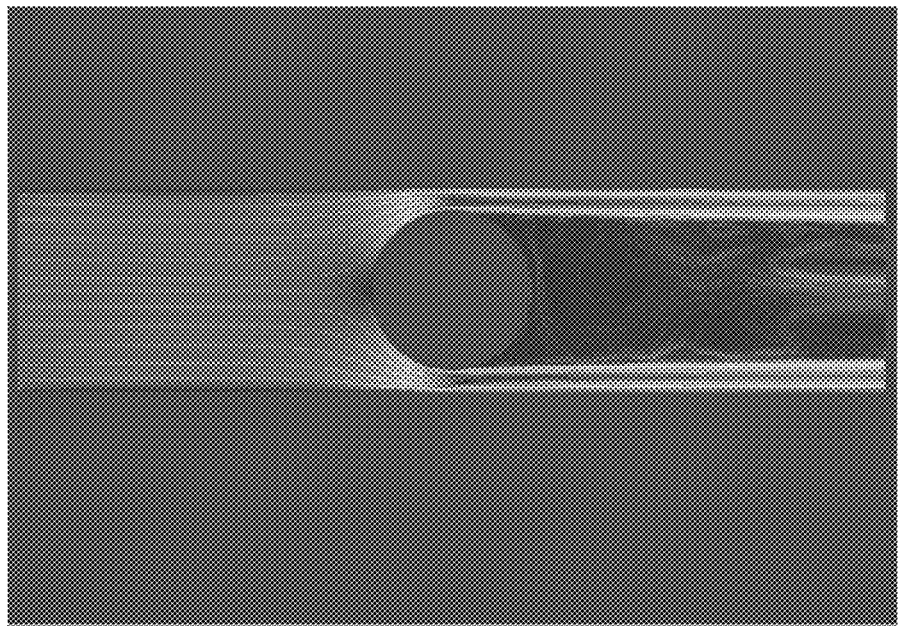
Figure 2A:
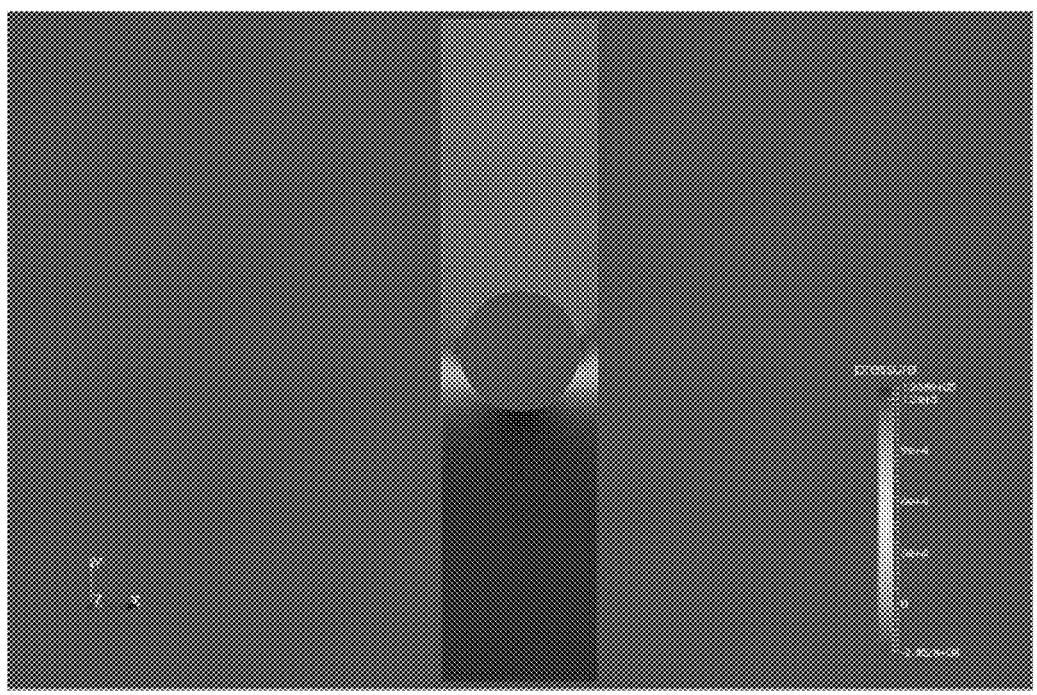
Figure 2B:
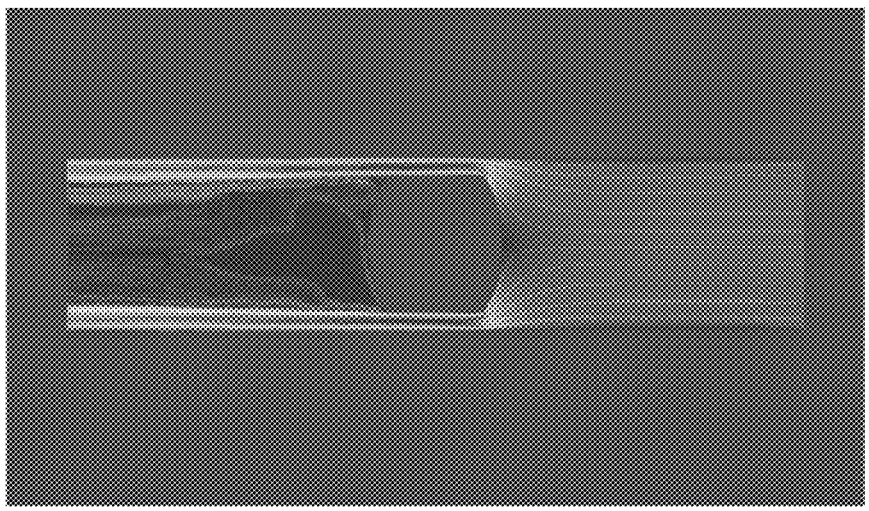
Figure 2B:
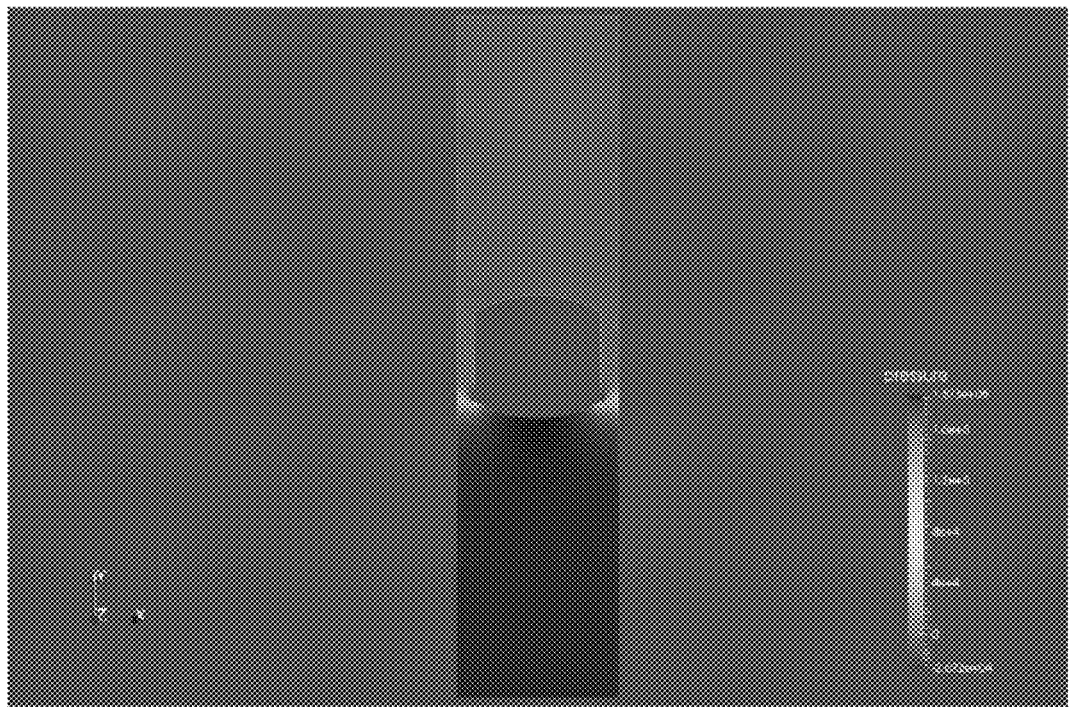
Figure 2C:
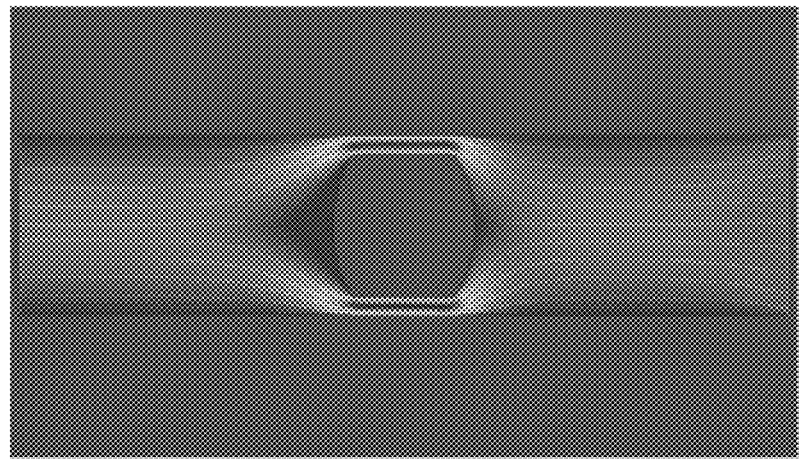
Figure 2C:
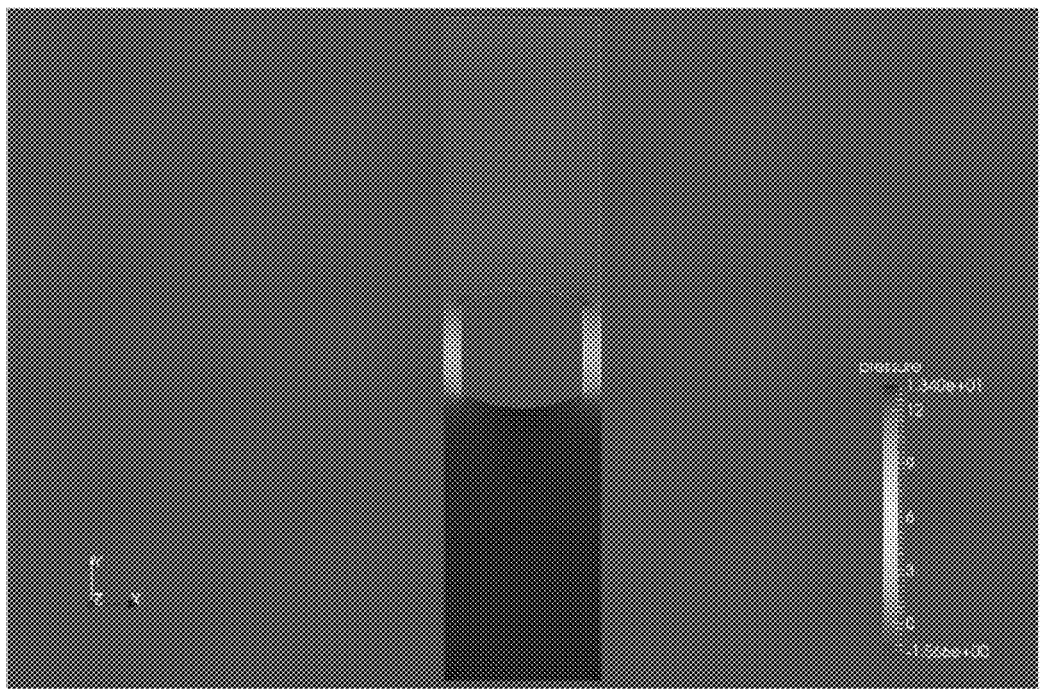

FIGS. 2A-2C include finite element analysis (FEA) modeling showing that a cylindrical bead, in fluid flow relative to such bead, can create qualitative differences in the nature of flow compared to a spherical bead, for a given level of certain quantitative stress parameters (e.g. duration, force/intensity).

DESCRIPTION

This section contains a range of descriptive content for this disclosure.

The present method involves using different bead-oscillation-based stress parameters, including bead dimensionality and shape, including non-spherical and substantially cylindrical, to induce qualitatively as well as quantitatively different stresses in samples upon bead movement (typically oscillation) in the sample. Other variable stress parameters may include overall stress magnitude as well as separated components thereof—such as duration and factors contributing to intensity. Depending upon the nature of the particular sample being tested, any subsequent analysis after the stressing may include a range of biochemical and/or biomechanical assays that could then aid in ascertaining the effects of any given combination of stress parameters upon respective samples run.

In at least some cases, bead design, particularly relative to the container/cartridge interior in which the sample resides during stressing/testing, can play a significant role in determining the relative contribution of turbulent and laminar flow based stress induced (apart from any absolute differences/changes in either or both types). By exploiting phenomena such as this, appropriate beads can be identified or produced, and employed in testing samples so as to create (or come usefully close to) stress conditions desired in a given instance.

A notable example application occurs with testing red blood cell (RBC) mechanical fragility (MF), in which a sample containing RBC is subjected to mechanical stress of defined amount(s) after which the level of hemolysis in said sample is measured to reflect the MF of the cell population. While turbulence and turbulence-induced mechanical stress has been well noted as a relevant factor in blood circulation, both in physiological conditions and when implantable medical devices are used (e.g. LVADs), laminar flow and associated stress also has significant physiological relevance in part due to its noted potential link to cell adhesion properties and cell interaction with endothelium. The ability to meaningfully control the relative or absolute degree and/or nature of turbulence, and/or add laminarity, and related stresses, in addition to overall stress magnitude control, has short-term utility as a research tool/technique (e.g. as an enhancement for more comprehensive MF testing) and potential long-term utility in medical product development or medical practice (potential areas of adoption in general for MF testing). [It could be expected that turbulent-type stress would result in fluid-related (bulk) deformation and stress to RBC membranes. On the other hand, laminar-type stress would more likely involve cell-wall interaction, possibly mediated through cell adhesion to the walls. Both effects would be significantly affected by the flow rate (speed)—e.g., for turbulent flow in the actual amount and type of turbulence (e.g. size and scope of resulting vortexes), and for laminar flow in the time/ability of cells to adhere to the walls and in the magnitude/scope of potential drag between cell membranes and the walls.]

Many sorts of approaches—such as concentric cylinders (e.g. Sutera 1972), orifice and capillary (e.g. Tamagawa 1996), rotating plates (e.g. Nichols 1976), convex/concave (e.g. Hashimoto 1989), bead agitation (e.g. Butler 1992), and other bead milling (e.g. Raval 2010)—have precedent for use in stressing RBC to cause cell lysis. Notably, these approaches induce different types of stress (or combinations thereof) with potentially different results relative to stability/fragility evaluation of cell membrane.

However, certain adaptations of bead mill based stressing show particular usefulness for providing a variable range of mechanical stresses that differ qualitatively as well as quantitatively. Such adaptations, unlike other bead-based approaches, can also include using non-spherical beads. This then relates to the shape of the bead/object used (e.g. sphere vs. cylinder), as well as other aspects such as size relative to tube diameter (e.g., if tube is cylindrical), tube length and other dimensions, and end-effects during oscillation.

If a given type of stress is applied to an RBC sample for multiple durations and/or intensities, a 2-dimensional or 3-dimensional fragility profile can be plotted (showing the dependency of hemolysis upon such stress parameter(s)) and various possible fragility index values can be determined therefrom (such as by interpolation, derivation, or other inference—possibly after regression curve fitting and/or other post-test processing as well). The more data points a collected profile has, the more accurate any polynomial-based or other regression will be in producing a generalized profile on which indices may be based. One such example index may be termed "S50," set as the duration of a given stress of a given type at a given intensity that corresponds to 50% hemolysis in a given sample; conversely, other indices may instead denote level of hemolysis corresponding to level of stress (e.g. "H50"). Other indices may include area under the curve, slopes/derivatives of profiles (whether interpolated, regressed, etc.) at particular points.

Protective effects of albumin on RBC have been reported for different approaches to stressing RBC, with varying results. Initial experimental data using the above approach in testing RBC MF shows that the protective effect of albumin on RBC (manifested in effectively slower lysis or lower MF) decreases when the fluid flow creating the mechanical stress involves oscillating a cylindrical bead rather than spherical (for a given set of other oscillation parameters such as frequency and force).

FIGS. 1A-1D contain preliminary experimental data regarding stress-induced RBC hemolysis, discussed following.

FIG. 1A shows the dependence of the efficiency of hemolysis (under stress) on the length of the bead/insert, with the bead/insert length being presented as the fraction/percent of the internal lysing chamber length that it occupies.

If BL is the length of the bead/insert and CL is the internal length of the lysing chamber, then notably elevated hemolysis is observed in the range of ratios of BL/CL from about 0.4 to 0.9. Hemolysis efficiency can be maximized if the ratio BL/CL is in the range between about 0.5 and 0.8, with a more particular maximum at ratios of about 0.65-0.75. (Note that these are "all else equal" comparisons.)

The bead length can potentially be adapted to use a desired sample volume while maintaining high efficiency of hemolysis. Increased BL/CL fractions result in decreased sample volume (due to the increased volume of the bead occupying chamber space) and for a tested configuration such fractions allowed decreasing the sample volume required for testing by about 75 percent. This shows potential for selection of optimal volumes that may be desired for given applications with minimal loss of lysing efficiency. For example, in cases where sample volume is at a premium (e.g. pediatric patient samples), a maximum ratio may be selected, while in cases of research (where large samples need to be stressed for further processing) a smaller ratio may be selected.

Figure 1B:
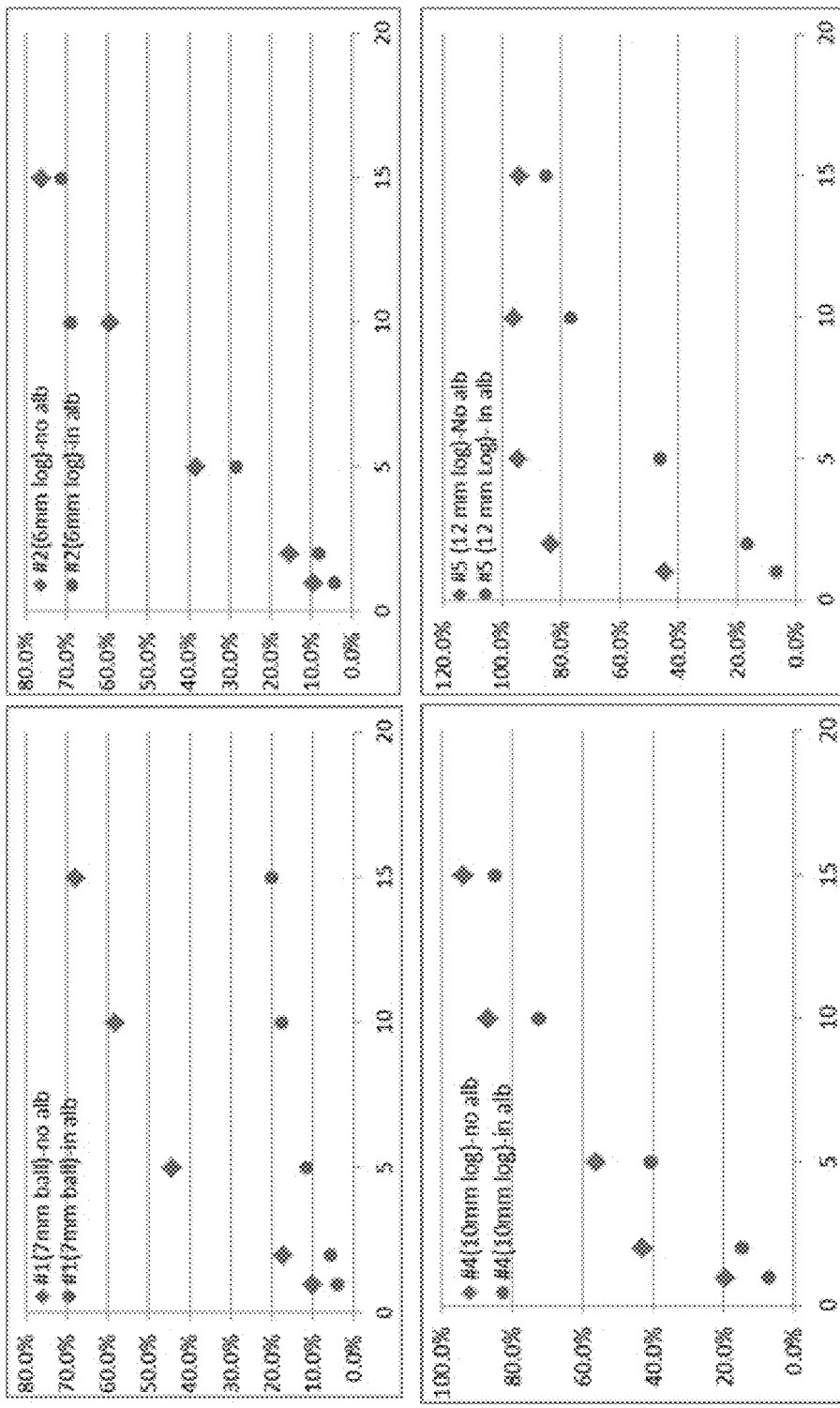

FIG. 1B illustrates the difference a bead's length (at a set tube length) can make on induced hemolysis as a function of stress duration in a bead mill (in minutes), not only in the overall magnitude (percentage hemolysis) for un-supplemented physiological or buffer media, but also in the extent of the protective effect of blood proteins (e.g. albumin) when such are present in the media. Top-left plot (when the four parts are viewed such that the labels read horizontally left-to-right) is with a sphere/ball for the bead, while the others are with cylinders/logs (of different lengths but same diameter).

Magnitude of hemolysis that results from stress application (at a given movement-inducing amplitude and oscillation frequency of the bead) depends significantly on cell environment or media. In particular, plasma had been shown to effect protection against (and thus comparatively reduce, all else equal) hemolysis induced by certain types of mechanical stress. This protective effect of plasma is due to the effects of plasma proteins. Albumin, fibrinogen and gamma-globulins had been shown to provide such protection to different extents, likely due to their interaction with RBC membranes. Albumin has the most pronounced effect, at least when stress is applied via the bead milling approaches described herein. However, the magnitude of such protection is dependent on the particularities of the application of the stress—even within overall the same lysing system. In that regard, comparison between hemolysis achieved on the same sample (e.g. RBC suspension or whole blood) with and without albumin (or alternatively, with and without plasma or other plasma proteins) can be used to differentiate between mechanical stresses that may differently stress the cell membrane (e.g. by "probing" different aspects of cell membrane structure).

Thus when stress is applied using a sphere ("ball") there is a significant difference between hemolysis magnitudes depending on whether the media was supplemented with blood proteins (such as albumin) or plasma vs when it was not so supplemented (top left plot or Bead "#1"). However when a similar stress (same amplitudes, oscillation frequency) is applied using a cylindrical bead ("log") 6 mm long (top right plot or Bead "#2"), there is no difference in induced hemolysis between albumin-supplemented and non-albumin-supplemented media. Even a short cylinder (as compared to the ball), with its relatively greater longitudinal dimension, results in predominantly stress type(s), and associated RBC membrane stressing/deformation, less affected by the presence of blood proteins. [However, increasing the length of the cylindrical bead significantly (bottom plots or Beads "#4" and "#5") can result in decreased speed of the bead within the chamber (e.g. less time for acceleration to occur and lower final speed for each oscillation), allowing the protective effect of albumin to manifest again—reflecting a change in the overall composition of mechanical stress types being applied to RBC.]

Figure 1C:
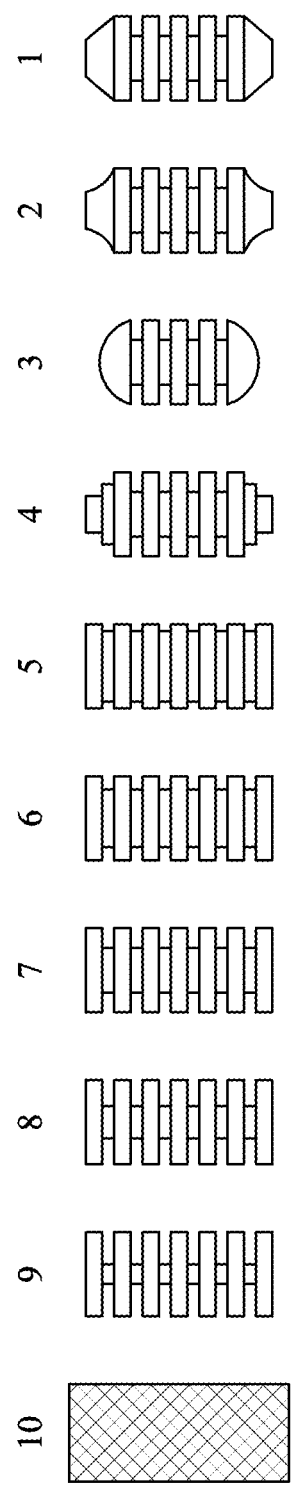

FIG. 1C shows examples of cylindrical beads with additional features, with the #s labelled 1-9 having grooves, and #10 having a knurled surface. Additionally, #s 1-4 have modified front ends including conical, combination/hybrid, spherical, and stepped end profiles (respectively), rather than a blunt end as in #s 5-10.

Additional modifications for example could involve the number and width of the ridges/grooves (not shown), and/or the depth of the grooves (e.g. as shown for beads #5-9, where the depth of the grooves ranges from 0.5 to 2.5 mm (corresponding to about 5-40% of the bead diameter in these cases), while the number and spacing of the ridges/grooves remain constant.) Note that here the grooves are orthogonal to the longitudinal dimension, but other orientations are possible for different effects. Note that the effect of having such adaptations means that the cross-section per se may not actually be cylindrical even in an otherwise cylindrical shaped bead (or the cross-section may be different at different points along the longitudinal axis).

The effect of such modifications to beads can enable additional opportunities to qualitatively vary the nature of overall stress or relative contributions of turbulence and laminarity, for example by changing the amount of surface area conducive to laminar flow and associated stress, or by introducing additional edges conducive to turbulent flow and associated stress. The extent of such effects involves an interplay between flow speed and bead features, for example sufficiently large orthogonal grooves for a given flow rate may create "pockets" in which fluid can enter and experience additional turbulence, as opposed to either essentially "skipping over" the groove or entering and exiting the groove while substantially preserving any otherwise present laminarity.

Figure 1D:
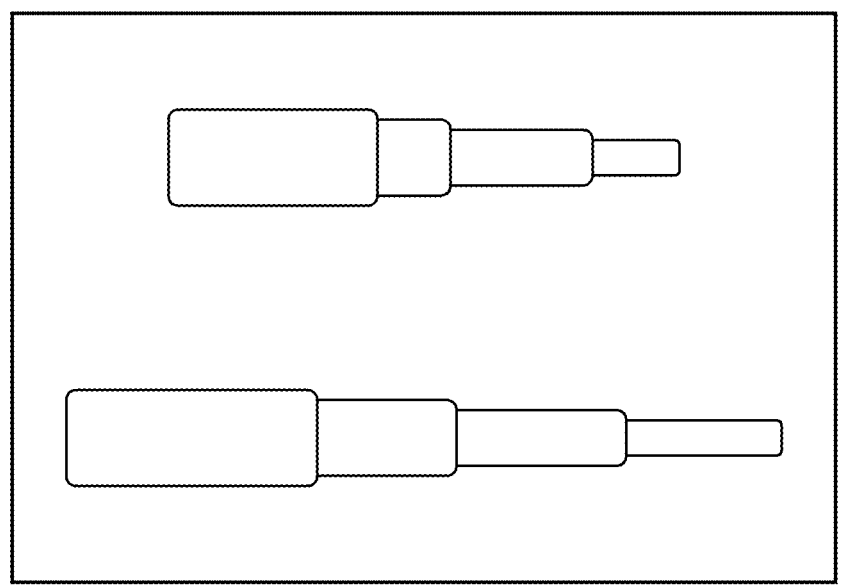

FIG. 1D shows an example of a composite "bead" that consists of a set of coaxial cylindrical tubes of different diameters that oscillate within the sample. Mechanical stress is induced by sample passing through the gaps between the cylindrical "rings." Such an arrangement could significantly reduce end effects of the flow, thus reducing overall turbulence, while increasing the influence of the surface of the "bead" (i.e. increasing lateral surface area) and overall laminarity. Notably, such a set of hallow cylinders (which incidentally could optionally include a central solid cylinder) could also employ textured surfaces and/or ridges/groves to further modify the flow.

Preliminary computational fluid dynamic (CFD) modelling of fluid movement relative to different beads shows that certain non-spherical bead shapes, such as at least some cylindrical shapes or the like, do indeed provide a different nature and pattern of flow overall than a spherical bead (all else being equal). Beads with ellipsoid, rectangular, or other cross sections can also be employed in elongated non-spherical shapes and may also result in similar phenomena—with or without correspondingly shaped tubes (also noting that non-cylindrical tubes could be employed regardless if desired)—and would provide relatively more surface area (compared to a sphere) in the longitudinal direction.

FIGS. 2A-2C contain preliminary computational fluid dynamic (CFD) results via finite element analysis (FEA) modeling, discussed following.

FIG. 2A shows a sphere moving relative to liquid, while FIGS. 2B and 2C show a cylinder of comparable overall size likewise moving relative to liquid (FIG. 2C being at a much lower speed than FIGS. 2A and 2B—i.e., 0.01 m/s vs. 3.1 m/s). In each of these three respective sets (FIG. 2A-2C), the upper image (i.e., the ones showing streamlines) shows a velocity gradient and the lower image shows a pressure gradient—while most of the following comments focus on the former. In both spherical and cylindrical cases shown, the bead's diameter is the vast majority of that of the tube.

In FIG. 2A, while there is some laminarity at the ends of the ball closest to the walls, the predominant effect of the ball moving through the liquid is to create turbulence in its wake. The cylinder shown in FIG. 2B likewise creates turbulence in its wake, but also has more high-speed laminar flow occurring proximate to the lateral surface of the bead—due to the relatively greater lateral surface area (where the laminar flow would be more intense, compared to the potentially extended laminarity shown in the wake, which appears similar between FIGS. 2A and 2B, but such wake-laminarity contributes much less to overall stress applied to the sample). Also, the fluid velocities appear faster (and thus stresses may be greater) around the cylinder vs. a sphere at a given bead velocity (i.e. FIG. 2B vs. FIG. 2A).

FIG. 2C shows the same cylinder as FIG. 2B but at a much slower speed, which shows that turbulence in the wake of the bead movement is far less, while high-speed laminar flow at the lateral surface of the bead (near the chamber/tube wall) still occurs.

This helps illustrate that relative amounts of turbulent and high-speed laminar flow can be manipulated or influenced using bead oscillation speed (with bead speed being a function of the bead's driving force intensity) as well as shape. Note that the above modeling data are highly preliminary, for conceptually illustrative use. Current limitations and assumptions include, for example, not accounting for end-effects of having tubes with finite length.

Regarding shape, longer beads can for example increase the surface area available for high-speed laminar flow (and associated stress), without necessarily changing the amount of turbulent stress (this must also take into account the effect on longer bead length on travel distance during oscillation between chamber ends, etc., but for some configurations and test parameters this may be sufficiently negligible). Alternatively, bead diameter relative to the diameter of the chamber could be set so as to influence the relative speed of the high-speed laminar flow along the lateral surface of the bead, with beads of larger diameter being associated with higher speeds and beads of smaller diameter with lower speeds.

The experimental and computational information disclosed above broadly reflect example utility of altering or controlling the overall flow, to create qualitatively different stress types (apart from changing certain quantitative stress parameters, or simply total stress magnitude), in enabling more expansive and comprehensive analysis and characterization of samples such as biological samples. This in turn can help, for example, with exploring and elucidating the natures and extents of protective effects from shear stress (during such stress) of substances such as albumin or other proteins on (and in the biochemical environment of) physiological components such as RBC.

An example of a stressing system employs an electromagnetically driven horizontal bead mill, whereby a magnetic bead in a sample-holding cartridge/container is shaken directly by an oscillating electromagnetic (EM) field without the cartridge itself being moved. Conveniently, there are commercially available coil based audio transducers fairly well adaptable to this purpose.

An example commercial EM actuator, by default, comes with a magnetically suspended piston that moves in precise response to amplified audio signal input; the mass can generate a high force that can be accurately transferred to whatever the housing is attached to, which makes it useful in its marketed uses of causing controlled vibration. As adapted, the piston is removed, and the cartridge is positioned inside the coil assembly such that the EM field directly moves the magnetic bead inside of the cartridge. Coil dimensions determine the optimal position ranges ("sweet spot") for cartridge placement and its chamber length to produce efficient bead movement, which are experimentally found.

Control of bead oscillation can be further exercised by the nature of the audio signal input applied. For example, a square-wave signal can produce electromagnetic field oscillation that may be preferable to a sinusoidal-wave signal, particularly if it is desirable to control "dead time" where the bead is at the ends of the tube between its movements (which can affect true duration of actual stress exposure). The profile of the driving EM field can also be used to control the acceleration profile of the bead.

To address heat generated by both the actuator and bead movement, fans and thermal baffles can be employed to maintain ambient room temperature for the sample. More active temperature control features can be added if specific temperatures are desired for testing.

An example sample-holding cartridge is transparent, facilitating sample insertion via a gel-loading-type pipette. Transparency can also be useful in cases where the same sample chamber is being used for stressing as well as an optical detection of the sample between stressing increments. A marked or etched fill-line can be employed to facilitate filling the chamber with reproducible sample volume. An example approach for loading is to go just under 100% of the cartridge's total fluid capacity, to facilitate consistency as well as avoid foam during bead movement. Alternative designs may instead target a slight overfill by the user, with residual going to a waste reservoir upon closing the cartridge. Inside the sample chamber (tubing interior) can reside a magnetic bead to be longitudinally oscillated between the two ends.

For the plastic tubing constituting an example of the sample chamber, possible priorities to facilitate the method's use in RBC MF analysis (particularly if involving direct optical measurement after stressing, without necessarily extracting the sample) may include optical transparency and sufficient thinness, as well as a balance of softness (to compress easily to achieve a desired sample thickness, as a way to facilitate use with optical detection of sample while it remains in the same chamber) with resilience (to spring back after each pinch or compression, and to not fatigue to a point of affecting results significantly, for uses involving multiple iterations of stressing and detection for a given sample). The transparency of the tubing/chamber for such a use should be sufficient to allow detection of an absorption spectrum of hemoglobin (Hb) and/or cell-counting, to allow ascertainment of hemolysis. Clear medical-grade Tygon® tubing has been found acceptable.

Because using direct magnetic bead movement limits possible bead materials, for doing blood testing the method benefits from having a biocompatible bead coating to prevent unacceptable levels of inter-conversion between hemoglobin (Hb) forms (i.e., from oxyHb to deoxyHb and metHb) during stressing. It is also important that the bead's exterior, including any coating it may have, can withstand the repeated impacts during oscillation of hitting the tube's end-caps or plugs or whatever other barriers may be present to seal or enclose the tube (without incurring damage that would affect results), at least through one typical run— before the cartridge/bead may be disposed. Black epoxy coating was found acceptable both from the biocompatibility and from the durability points.

Cartridges for holding the sample and bead/object can be fully or partially disposable, with examples of the latter including having flexible plastic tubing be detachable and replaceable by a user between runs or tests (while a cartridge body structure may be rigid). In such cases, kits may be provided that may include precision-cut tube length (for consistent effects from run to run) and possibly replacement bead(s) as well. In some embodiments, it is preferable to use flexible cylindrical plastic tubing that is cut to a length with tolerances on the order of 0.1 mm (which is unusually tight, but feasible with appropriate machinery—particularly if a sufficient scrap rate is tolerated based on measured resulting length). Though conceivably the tube/tubing segment and/or the bead may be washable for reuse, that can be suboptimal in terms of quality assurance and convenience, plus those components are susceptible to wear which can affect results over sustained use. When using a fully-disposable cartridge (structural body as well as stressing chamber and bead), quality, convenience, and safety advantages are all the greater. Also, in applications where compression of the tube is not needed, a rigid tube or the like could be employed instead of a flexible one.

Potentially, cartridges could be provided/offered with different bead(s), facilitating bead selection being another testing variable (in addition to oscillation frequency and magnetic force). Important to characterize for any given cartridge/container being used are the relative and interrelated contributions of a bead's own design and the various oscillation parameters to the fluid dynamics of the stressing—and potential effects of such on the sample in question, which may in turn depend on sample preparation such as dilution or normalization of any relevant concentrations (such as RBC concentration, if testing RBC MF for example).

Following below are select descriptions of an example bead-mill system and cartridge, corresponding (respectively) to FIGS. 25 (A-C) and 27 (A-B) of WO/2014/137499, the disclosure of which is hereby incorporated by reference in its entirety. Those depictions, in light of the above information, suffice to show relevant hardware that can be employed for the present method and associated materials. In that example testing setup, the cartridge can be fully replaceable, or just the tubing (stressing chamber) can be replaceable between uses, possibly along with the bead. (If the main structure or body of the cartridge is being reused, a suitable material for it is acetal polyoxymethylene (e.g. Delron), with the plug portions and other relevant aspects being designed and machined so as to be suitable for enabling a disposable flexible tube segment to be put on and taken off by a user between uses.)

In the example cartridge embodiment depicted, the overall cartridge includes a cartridge body featuring ventilation holes and a capturing hook for attaching to the machine (described below). Said body holds/contains a piece of pre-manufactured flexible clear tubing of appropriate thickness to be sufficiently compressible and resilient, which provides a sample cavity. Barbed plugs are on each end of the tube, confining a coated magnetic bead, in this case cylindrical, with the "top" one of said plugs being hollowed to provide a capillary for inserting the sample (e.g. via pipette tip, such as used for loading electrophoresis gels) before the sealing plug is secured (e.g. via screw-threads). Upon pinching at the cavity area between successive intervals of milling, sample inside is temporarily pushed away from the light path as part of the tubing shape gets reversibly compressed to allow taking an optical reading through said tubing (if desired). There may also be a separate window to facilitate calibration or base-lining (not shown), which alternatively could be located on the machine itself.

In the example bead miller embodiment, which employs a "direct" magnetic-bead approach that avoids having to shake the entire cartridge, a low-frequency audio transducer serving as an electromagnetic bead actuator essentially is adapted from a commercially-available item. (By default the item comes with a magnetically suspended piston that moves precisely in response to amplified audio signal input; the mass can generate a high force that can be accurately transferred to whatever the housing is attached to (which is more relevant for the "cartridge-shaking" embodiments, rather than the direct "bead-moving" embodiments.) For embodiments wherein the cartridge is stationary and the bead is moved by direct magnetism, the cartridge is positioned such that the magnetic bead inside of the cartridge is directly movable by the transducer. Bead mills may be multi-plexed to allow several samples to be milled simultaneously; this can be done by using multiple of such audio transducers or other coil-based EM actuators, and/or the direct "bead-moving" approach by placing multiple tubes in the EM "sweet spot" (the particular location and size of which depends upon the particular configuration employed) where the field causes magnet oscillation. And of course, for just a plain bead mill without fragility testing, no flexible or "pinchable" portion for pinching/compressing is needed in the tube(s). Because the bead miller version here is specifically designed to be incorporated in a fragility-testing machine, in an embodiment designed to incorporate a commercially-available EM actuator, it also has a cartridge carrier that slides along a cartridge rail as driven by a cartridge loading motor, to provide movement of the cartridge(s) to and from the region of bead actuation/movement (to and from the region of optical detection, after respective stressing intervals). A thermal baffle may be employed to direct air flow from fan(s) (not shown), as desired (note that temperature is more often a concern with fragility-testing versus with plain bead-milling).

The present disclosure as a whole, including any drawings or claims, contains content not necessarily limited to any particular embodiment or example or features thereof in any given portion or aspect of the disclosure. Any use herein of terms such as "the invention" and the like are likewise not necessarily intended to be limiting. The scope of any patent(s) granted regarding the disclosure is to be defined by the claims as issued.

We claim:

1. A method of inducing controlled flow in a biological sample containing a whole blood component through bead oscillation, comprising:
   placing the biological sample in a container;
   selecting a first bead from among a plurality of beads, each bead of the plurality of beads inducing in the biological sample at least one of a different predetermined flow turbulence or a different predetermined flow laminarity relative to every other bead in the plurality of beads to thereby induce in the biological sample a different predetermined stress from among a plurality of predetermined stresses when oscillated within a container housing the biological sample;
   placing the first bead in the container; and,
   oscillating the first bead within the container to induce a first predetermined stress in the biological sample
   wherein the first bead has a non-spherical shape.

2. The method of claim 1, further comprising the step of selecting a bead oscillation speed for the first bead based on a predetermined influence of the bead oscillation speed on flow turbulence or flow laminarity and wherein the oscillating step includes oscillating the first bead within the container at the bead oscillation speed.

3. The method of claim 1 wherein said first bead is magnetic and said oscillating step includes applying electromagnetic fields to the first bead to oscillate the first bead.

4. The method of claim 1 wherein said container comprises a tube.

5. The method of claim 1 wherein the sample contains red blood cells (RBC).

6. The method of claim 5, further comprising the step of measuring, after oscillating, hemolysis in the sample to determine RBC mechanical fragility.

* * * * *